United States Patent
Vallittu

[11] Patent Number: 5,846,640
[45] Date of Patent: Dec. 8, 1998

[54] POLYMER-FIBRE PREPREG, A METHOD FOR THE PREPARATION THEREOF AS WELL AS THE USE OF SAID PREPREG

[75] Inventor: Pekka Vallittu, Kuusisto, Finland

[73] Assignee: Bioxid Oy, Turku, Finland

[21] Appl. No.: 809,488

[22] PCT Filed: Feb. 19, 1996

[86] PCT No.: PCT/FI96/00095

§ 371 Date: Mar. 27, 1997

§ 102(e) Date: Mar. 27, 1997

[87] PCT Pub. No.: WO96/25911

PCT Pub. Date: Aug. 29, 1996

[30] Foreign Application Priority Data

Feb. 24, 1995 [FI] Finland ..................... 950844

[51] Int. Cl.⁶ ................................................ B05D 3/00
[52] U.S. Cl. .............. 428/306.6; 427/2.29; 427/195; 427/336; 427/389.8; 428/304.4; 442/180
[58] Field of Search ................ 442/180; 427/2.29, 427/195, 336, 389.8; 428/304.4, 306.6

[56] References Cited

U.S. PATENT DOCUMENTS

| | | | |
|---|---|---|---|
| 4,919,978 | 4/1990 | Winkler et al. | 427/381 |
| 4,954,304 | 9/1990 | Ohtake et al. | 264/137 |
| 5,011,721 | 4/1991 | Decker et al. | 428/36.9 |

FOREIGN PATENT DOCUMENTS

| | | |
|---|---|---|
| 1115544 | 5/1968 | European Pat. Off. . |
| 27 49 564 | 10/1979 | Germany . |
| 1584530 | 2/1981 | United Kingdom . |
| WO 91/10547 | 7/1991 | WIPO . |
| WO 91/11153 | 8/1991 | WIPO . |

OTHER PUBLICATIONS

International Preliminary Examination Report for PCT/FI96/00095.

*Primary Examiner*—James J. Bell
*Attorney, Agent, or Firm*—Adduci, Mastriani, Schaumberg, L.L.P.

[57] ABSTRACT

The invention relates to a method for the preparation of the fibre product pre-impregnated with a polymer (prepreg) where the method includes: a) coating the fibres with a powder comprising at least one polymer and optionally an agent having the ability to initiate the polymerization reaction of the polymer, b) adding to the composition obtained in step a) a solvent possessing the ability to dissolve the polymer but lacking the ability to initiate the polymerization reaction of the polymer, and c) evaporating the solvent. Alternatively, the polymer (optionally including the initiating agent) can first be dissolved in the solvent after which the fibres are contacted with the solution thus obtained and the solvent is evaporated. The surface of the fibres is preferably treated so as to facilitate the bonding of the polymer to the fibres, whereafter the surface treated fibres are coated with the polymer powder. The invention relates further to a novel prepreg, a method for the manufacture of fibre reinforced composite based on the use of the prepreg, the novel composites and their use.

19 Claims, 3 Drawing Sheets

POLYMER-FIBRE PREPREG, A METHOD FOR THE PREPARATION THEREOF AS WELL AS THE USE OF SAID PREPREG

FIELD OF THE INVENTION

The present invention relates to a method for the preparation of a fibre product pre-impregnated with a polymer (prepreg). The invention relates further to a novel prepreg, a method for the manufacture of fibre reinforced composite based on the use of said prepreg, the novel composites and their use.

BACKGROUND OF THE INVENTION

The publications and other materials used herein to illuminate the background of the invention, and in particular, cases to provide additional details respecting the practice, are incorporated by reference.

Dental devices made from polymers are prone to fracture in the oral conditions. For instance, it is well documented that a removable denture can fracture after the denture has been worn for some years, (1–4). Consequently, an ideal reinforcement of a denture should be used both in the fabrication of a new denture and in repairing of an old denture. The polymer devices and constructions in dentistry have traditionally been reinforced with metal inclusions of the polymer (5–7). The effect of the metal inclusions in the strength of the polymer device or construction is, however, inadequate. Attempts have been made to develop a polymer-fibre composite which can easily be used as reinforcement of dentures. Before the date of the present invention, no fibre-composite products fulfilling the requirements of the clinical dentistry and the dental laboratory technology have been achieved, even though one fibre ribbon product exists on the market for use in dentistry (Ribbond®, Ribbon Inc., Seattle, Wash., U.S. Pat. No. 5,176,951).

Known polymer-fibre composites for prosthetic dentistry have been made by dipping the fibre bundle, ribbon or weave in methylmethacrylate (MMA) monomer or in a mixture of polymethylmethacrylate (PMMA) powder and its monomer (MMA). Composites made by this method are, however, not suitable for use in dentures because of the following shortcomings:

1) inadequate adhesion between the PMMA and the fibres, especially with PMMA to be used in denture repairing, i.e. autopolymerizing PMMA (8),
2) inadequate impregnation of fibres with PMMA (9–11),
3) spreading of the fibres to undesired regions of the denture during compression moulding of the PMMA (12),
4) difficult handling of the fibres in the dental laboratory (13), and
5) mechanical irritation of the oral soft tissues due to the protruded fibres on the denture surface (14).

Attempts have also been made to manufacture a pre-impregnated fibre bundle with a polymer (which is called a polymer-fibre prepreg). Three general methods for the manufacture of such thermoplastic polymer-fibre prepregs have been reported (15):

1) an in situ polymerization method, which is a resin injection method whereby the monomer is incorporated into a fibrous preform,
2) a film stacking method in which layers of fibres are laminated between layers of polymer film, and
3) a powder coating method in which fibres are impregnated with polymer powder which is then melted.

These methods have, however, some shortcomings in terms of dental requirements. The in situ polymerization, even though it can be used with PMMA, results in a composite having polymerization shrinkage voids in the structure, wherein said voids will be filled with saliva and oral microbes. The film stacking method yields a composite with poor degree of impregnation (i.e. the fibre bundle is not sufficiently impregnated by the polymer). The insufficient degree of impregnation will also cause voids in the structure of the composite. The powder coating method includes melting of the polymer powder. This method results in a prepreg of a dense structure which is difficult to plasticize before the usage by dissolving the polymer. Consequently, any of the methods used in general plastic industry to produce fiber composites are not suitable for use in fabrication or repairing of dentures.

OBJECT AND SUMMARY OF THE INVENTION

The requirements imposed by clinical dentistry and dental technology on a prepreg useful in dentistry reinforcement are the following:

1) the prepreg must be easy to form into the shape of anatomical structures of the oral cavity, i.e. the prepreg should be plastic at room's temperature when used in denture fabrication or repairing,
2) the prepreg must retain its shape to allow the covering of the prepreg with unfilled (i.e. fibre free) polymer,
3) the polymer of the prepreg should polymerize simultaneously with the surrounding polymer,
4) the polymer matrix should react chemically with the surrounding polymer, irrespective of whether it is a heat-curing polymer or an autopolymerizing polymer, and
5) the fibres of the prepreg should adhere to heat-curing polymer as well as autopolymerizing polymer.

One object of the invention is a prepreg fulfilling the aforementioned requirements 1) to 5).

Another object of the invention is the use of said prepreg in the manufacture of fibre reinforced composites. Said composites are suitable for use in any technical field, particularly in the dental or medical field.

Thus, according to one aspect of the invention a method is provided for the preparation of a fibre product pre-impregnated with a polymer (prepreg). Said method comprises either i)
a) coating the fibres with a powder comprising at least one polymer and optionally an agent having the ability to initiate the polymerization reaction of said polymer,
b) adding to the composition obtained in step a) a solvent possessing the ability to dissolve said polymer but lacking the ability to initiate the polymerization reaction of said polymer, and
c) evaporating the solvent, or ii)
a) dissolving a powder comprising at least one polymer and optionally an agent having the ability to initiate the polymerization reaction of said polymer into a solvent possessing the ability to dissolve said polymer but lacking the ability to initiate the polymerization reaction of said polymer, and
b) contacting the fibres with the solution obtained in the foregoing step, and
c) evaporating the solvent.

Although the prepreg can be manufactured in the form of a continuous web it is in many fields of use preferable to manufacture the prepreg readily shaped into its desired form. In this case the composition obtained in step a) is added to a mould before the solvent is added. After the evaporation the finished prepreg is removed from the mould.

According to a preferred embodiment, the surface of the fibres has been treated so as to facilitate the bonding of the polymer to the fibres, whereafter the surface treated fibres are coated with the polymer powder. Preferably, an agent facilitating the bonding of the polymer to the fibres has been applied onto the fibre surface before the fibres are coated with polymer powder.

According to another aspect the present invention provides a porous prepreg comprising of fibres and a polymer wherein said polymer is present between the individual fibres and has been distributed between the fibres as a solution from which the solvent has been evaporated.

In a particularly preferable prepreg the fibre is a glass fibre, the polymer is polymethyl methacrylate (PMMA), ethyleneglycoldimethacrylate (EGDMA), 2,2-bis[4-(2-hydroxy3-methacroyloxy)phenyl]-propane (BIS GMA), or hydroxy-ethylenemethacrylate (HEMA), and a silane compound, preferable gamma-methacryloxypropyl-trimethoxy-silane, has been applied onto the surface of the fibre.

According to yet another aspect the present invention provides a method for the manufacture of a fibre reinforced composite based on the use of the prepreg according to this invention. Said method comprising the steps of adding a plasticizer to the optionally pre-formed prepreg, shaping the plasticized prepreg into the desired form, embedding the prepreg into the plain polymer of the composite, or into a mixture of said polymer and the monomer, and allowing the polymer of the prepreg to polymerize simultaneously with the plain polymer of the composite.

The reinforced composite can be used as such or, alternatively, be used as starting material for the manufacture of blocks of desired shape. Thus, a dental composite can e.g. be machined into dental restorations and dental and medical implants.

According to another preferred embodiment, the polymer of the prepreg is the same as the unfilled polymer of the composite.

The invention further provides a fibre reinforced composite comprising a prepreg according to this invention. Said prepreg has been plasticized by wetting with a monomer, shaped into the desired form and embedded into the plain polymer of the composite, and the polymer of said prepreg has been allowed to polymerize simultaneously with the plain polymer of the composite.

Said composite can be used in any technical application. It is, however, particularly suitable for use in medical or dental constructs such as prosthodontic, orthodontic or orthopaedic appliances; removable denture frameworks, removable denture clasps or precision attachments; permanent or temporary fixed prostheses including tooth and implant supported prostheses; dental or medical implants; rooth canal fillings of endodontically treated tooth; posts, cores, fillings or crowns of the tooth, mouth guards, and the like.

DETAILED DESCRIPTION OF THE INVENTION

Figures 1A, 1B, 1C:
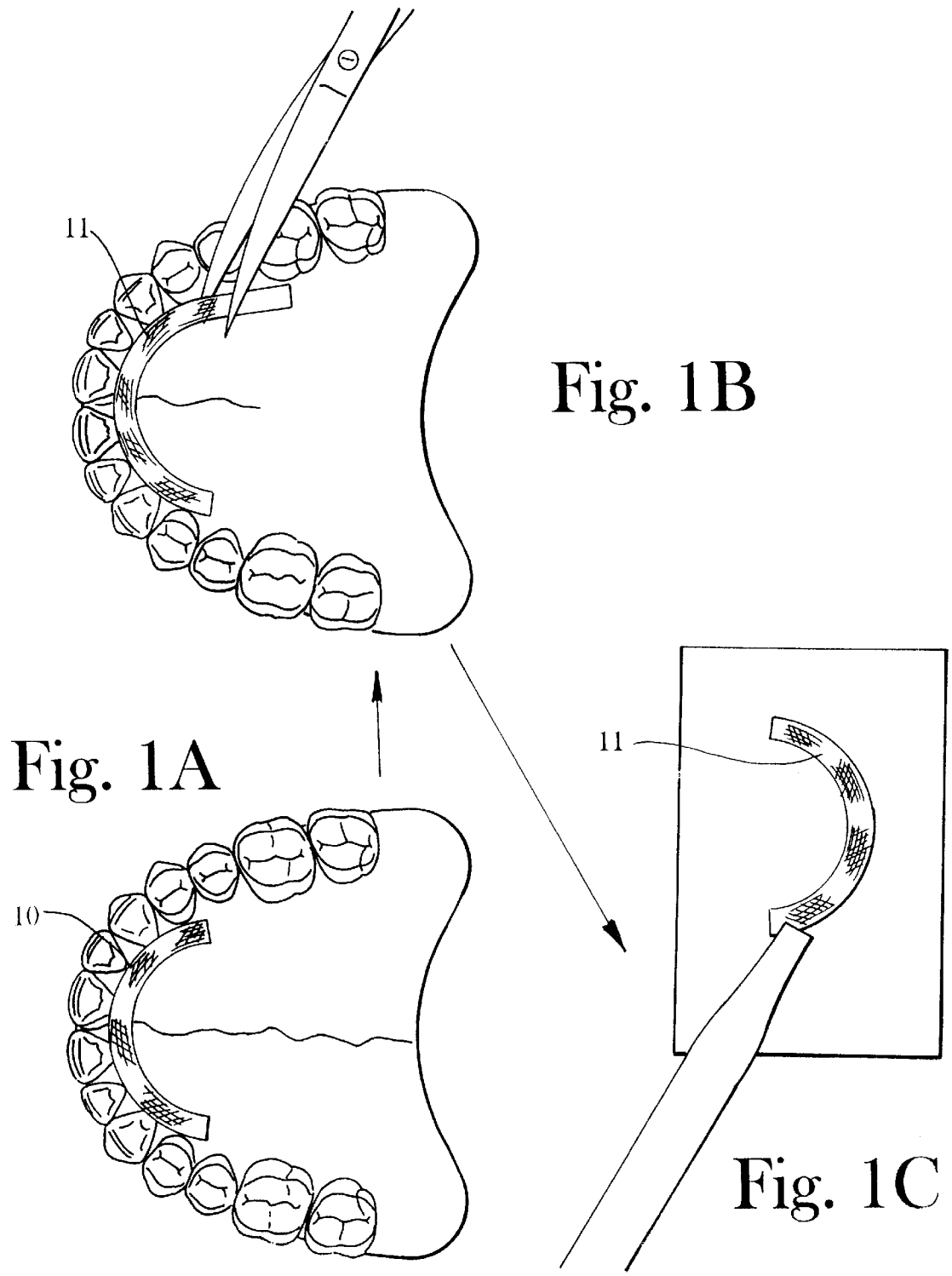
FIGS. 1A to 1C demonstrate the use of the prepreg in the repairing of a complete denture.

Suitable fibres for use in this invention are either inorganic or organic fibres. The choice of fibre depends highly on the technical field in which the fibre reinforced composite shall be used. Fibres already tested in dentistry as reinforcement of dentures include E-glass (electrical glass) fibres (10), S-glass (high strength glass) fibers (16), carbon/graphite fibres (12, 17, 18), aramid fibres (19) and ultra-high-modulus polyethylene (8, 13, 20–23). The black colour of the carbon/graphite fibres make them less suitable for dental use. Organic fibres have been reported to cause inadequate adhesion to dental dental polymers (8). It seems therefore that glass fibres best fulfill the cosmetic and adhesive requirements for dental use.

The fibres can occur in various forms. As examples can be mentioned rovings, woven rovings, woven mats, chopped strand mats, whiskers or as fibre particles (fillers). The choice of fibre product depends on the intended use of the composite. Mixtures of the various fibre forms can also be used.

The polymer of the prepreg can be any polymer. For medical and dental use a thermoplastic polymer material is preferred. Preferably, the polymer of the prepreg is the same as the polymer surrounding the prepreg in the finished composite. A preferable polymer for use in dentistry is polymethyl methacrylate (PMMA), either heat-curing or autopolymerizing PMMA. Heat-curing PMMA is polymerized on water bath at temperatures in the range of 70° to 100° C. The polymerization is initiated by an initiator such as benzoyl peroxide (24). Heat-curing PMMA can also polymerized by microwave energy. Autopolymerizing PMMA is polymerized at lower temperatures (35° to 50° C.) than heat-curing PMMA and therefore a chemical compound, such as dimethylparatoluidine, is required to activate the initiator of the reaction (24). Among other preferable polymers can be mentioned e.g. ethyleneglycoldimethacrylate (EGDMA), 2,2-bis[4-(2-hydroxy-3-methacroyloxy)phenyl]propane (BIS GMA), polyethylene-terephtalateglycol (PETG), poly 1,4-cyclohexylendimethyleneterephtalateglycol (PCTG), hydroxyethylenemethacrylate (HEMA) or the like.

The proportion between the amount of fibres and polymer should preferably be chosen so as to give good porosity of the prepreg after the solvent has been evaporated. High porosity is advantageous because it enables an easy penetration of the prepreg by the plasticizer. When glass fibres and PMMA are used, the best porosity is obtained when equal amounts of fibres and polymer are used.

The surface of the fibre can optionally be prepared to facilitate the bonding of the polymer to the fibre either physically or chemically, e.g. by use of an agent. The choice of the agent facilitating the bonding of the polymer to the fibres (i.e. the coupling agent) depends on the fibres and polymer matrix used. In dentistry, common coupling agents for improving the adhesion between the glass fibres and PMMA are silanes. A particularly preferred silane compound is gamma-methacryloxypropyltrimethoxysilane (MPS). Adhesion between carbon fibres and the polymer matrix can be improved by oxidative or irradiation methods as well as with silane compounds. Polyethylene fibres can be made more adhesive to the polymer matrix e.g. by plasma etching of the fibre surface. The results obtained thereto have, however, been rather poor (21).

According to a preferred embodiment of the present invention, the coupling agent is precured onto the fibre surface before the fibre is contacted with the polymer. This enables the use of heat-curing polymers as well as autopolymerizing polymers. According to known methods, the curing of the silane compound occurs simultaneously with the polymerization of the heat-curing PMMA. There are no reports on successful use of silanes for improving the adhesion between autopolymerizing PMMA and glass fibres.

The initiator of the polymerizing reaction is e.g. added either to the polymer material of the prepreg or to the plasticizer used to plastize the prepreg before its use. The initiator can be any suitable known polymerizing initiator. Most common initiators are peroxides, e.g. benzoyl peroxide.

The solvent used in the preparation of the prepreg can be any solvent having the ability to dissolve the polymer material but lacking the ability to initiate the polymerization reaction thereof. Tetrahydrofuran (THF) is an example of a suitable solvent. The dissolution of the polymer material and subsequent evaporation of the solvent results in a very good polymer impregnation of the fibre product, which in turn, as will be disclosed in the examples, results in excellent strength properties of the finished composite. The solvent should preferable evaporate rather quickly because this facilitates a porous structure of the material in the prepreg.

As plasticizer to be used to plasticize the prepreg can be used a monomer, either the monomer of the polymer powder included in the prepreg, or a different monomer. Preferably the same monomer is used. In case the polymer is PMMA the monomer will thus be MMA.

The invention is illustrated by the following examples. In the examples the invention is explained in terms of its preferred embodiments and applications in prosthetic dentistry even though the invention also has other medical and technical applications.

Example 1

Preparation of the prepreg

E-glass fibres (Ahlstrom, Karhula, Finland) in continuous unidirectional roving form were cleaned by 1.5 mol/l sulphuric acid ($H_2SO_4$), washed with distilled water and then dried for 48 hours at +22° C.

The surface of the fibres was treated with gamma-methacryloxypropyltrimethoxysilane (MPS) (A174, Union Carbide Chemicals, Versoix, Switzerland) for improving the adhesion of the polymer (PMMA) onto the fibres. The dilute MPS (30% MPS, 70% methanol) was precured to the glass fibre surface at +100° C. for two hours. Additionally, commercially surface-treated glass fibres can be used.

The silane treated glass fibres were coated with dental heat-curing polymethylmethacrylate (PMMA) powder (Pro Base Hot, Ivoclar, Schaan, Liechtenstein) which included benzoyl peroxide as initiator of the polymerization reaction. The weight of PMMA powder used was equal to the weight of the glass fibres.

A desired amount of powdered glass fibres were placed into a mould having a cavity corresponding to the shape of the prepreg. The powdered fibres were wetted with tetrahydrofuran (THF), a solvent which dissolved the PMMA but which did not initiate the polymerization reaction of the dissolved PMMA. In this step the dissolved PMMA bonded the individual fibres together to form a rigid prepreg of predeterminated shape. The solvent (THF) was allowed to evaporate. Finally the prepreg was removed from the mould and packed for future use.

Another method to fabricate the prepreg is to dissolve a desired amount of PMMA into the THF, and dip the fiber rowing or weave in the mixture or pull the roving or weave through the mixture. The ratio PMMA to THF should be optimized to produce porous glass fiber—PMMA prepreg which can easily be wetted and plasticized with the MMA when the prepreg is used.

A prepreg based on autopolymerizing PMMA (Pro Base Cold, Ivoclar, Schaan, Liechtenstein) was manufactured in the same way as described above.

Example 2

The use of the prepreg as a reinforcement in denture manufacture

An acrylic resin based denture was made from heat-curing PMMA using compression moulding technique. The weak regions of the denture were reinforced with the prepreg from Example 1 as follows:

1) After trial packing of PMMA into a denture mould a concavity was pressed into the PMMA dough by using as space-maker a plastic strip of the same size as the prepreg.
2) The prepreg was plasticized by wetting it with the monomer of the heat-curing PMMA and placed into the concavity of the acrylic resin dough.
3) The final packing of the acrylic resin dough was carried out according to usual methods in dentistry (25).
4) The polymerization of the PMMA of the prepreg occurred on water bath simultaneously with the polymerization of the PMMA dough. The final product thus obtained was a denture comprising an orientated continuous fibre reinforcement coated with a layer of unfilled PMMA.

Example 3

The use of the prepreg in denture repairing

Figure 2A:
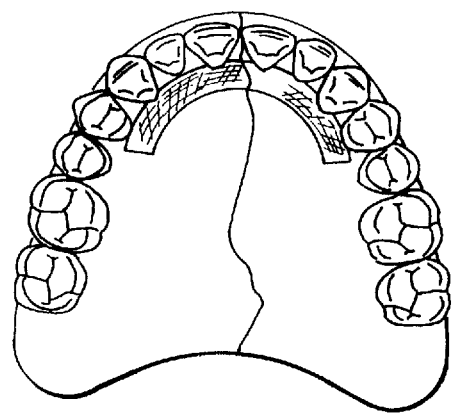
FIGS. 2A and 2B show two examples of fiber orientation in repaired dentures (FIG. 2A is a complete denture and FIG. 2B is an upper partial denture)
Figure 2B:
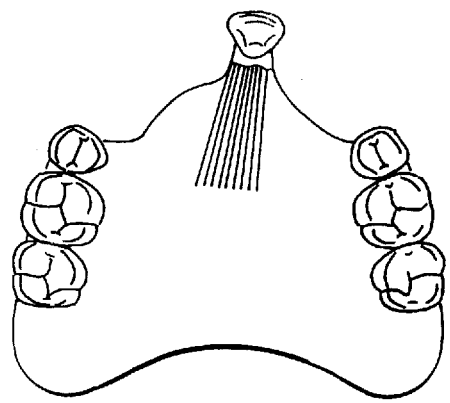

A fractured denture on a dental cast was shaped for repairing as described in the dental literature. Furthermore (see FIG. 1A–1C), a groove 10 of the same size as a prepreg 11 made of autopolymerizing PMMA and glass fibres was ground into the desired region of the denture. The prepreg 11 was plasticized (FIG. 1C) by wetting with the monomer of the autopolymerizing PMMA and placed into the groove of the denture. The groove was then filled with autopolymerizing PMMA which was allowed to polymerize on water bath simultaneously with the polymerization of the PMMA of the prepreg. A repaired denture reinforced with orientated fibres was thus obtained (see FIG. 2A–2B).

Example 4

The use of the prepreg as frame material of a removable denture

A prepreg was plasticized with the monomer of the polymer matrix. Then the prepreg was placed on the dental cast covering the region of the framework. The prepreg was positioned so as to give a fibre direction orientated against the predicted fracture line of the denture. The surface of the prepreg was coated with PMMA powder to cover the fibres with unfilled PMMA. Alternatively, the surface of the prepreg could be coated with a mixture of PMMA powder and MMA liquid (i.e. PMMA dough). The cast was placed into the curing unit for the polymerization of the PMMA. After curing a composite frame was obtained. Said composite frame can be used as a conventional metal frame in the manufacture of a removable denture.

Example 5
The use of the prepreg as a removable denture clasp

A prepreg, made into the shape of a denture clasp and into the colour of the tooth, was plasticized by the monomer of the polymer matrix (PMA). The plasticized prepreg was placed onto the desired region on the dental cast and it was bonded to the extension base of the removable denture. The prepreg was coated with tooth coloured PMMA powder before polymerization in the curing unit. Alternatively, the prepreg could be coated with tooth coloured PMMA dough before polymerization.

Example 6
The use of the prepreg in the fabrication of permanent, semipermanent or temporary fixed prosthesis The prepreg comprising of colourless or tooth coloured PMMA (or alternatively polybutylmethacrylate or polyethylmethacrylate or the like) was plasticized by the monomer of the polymer matrix. The plasticized prepreg was placed into a silicon mould of the fixed prosthesis which had been partly filled with the PMMA dough. The plasticized prepregs were then covered with the PMMA dough, and the mould was placed on the gypsym cast of the abutment teeth. After curing the PMMA, the fixed prosthesis was finished with the normal dental laboratory procedures.

The fixed prosthesis consists of either unidirectional glass fiber reinforcement which increases the strength of pontics and their joints to crown units, and additionally of glass fiber weave reinforcement, or short fibre reinforcement, which enhances the strength of the crown units and the fixed prosthesis.

Example 7
Properties of the fibre composites obtained

The methods described in prior art, i.e. dipping the fibre bundle into a mixture of PMMA powder and its monomer, give a degree of impregnation (amount of dental PMMA/amount of continuous unidirectional E-glass fibres) varying from 0.4 to 0.8. The degree of impregnation was lower for fibre rovings of higher specific amounts of fibres. The degree of impregnation of the composites made of continuous E-glass fibres and PMMA by using prepregs according to the present invention was 0.91 for heat-curing PMMA and 0.98 for autopolymerizing PMMA. Furthermore, the degree of impregnation was not affected by the specific fibre amount of the fibre roving.

Figure 3:
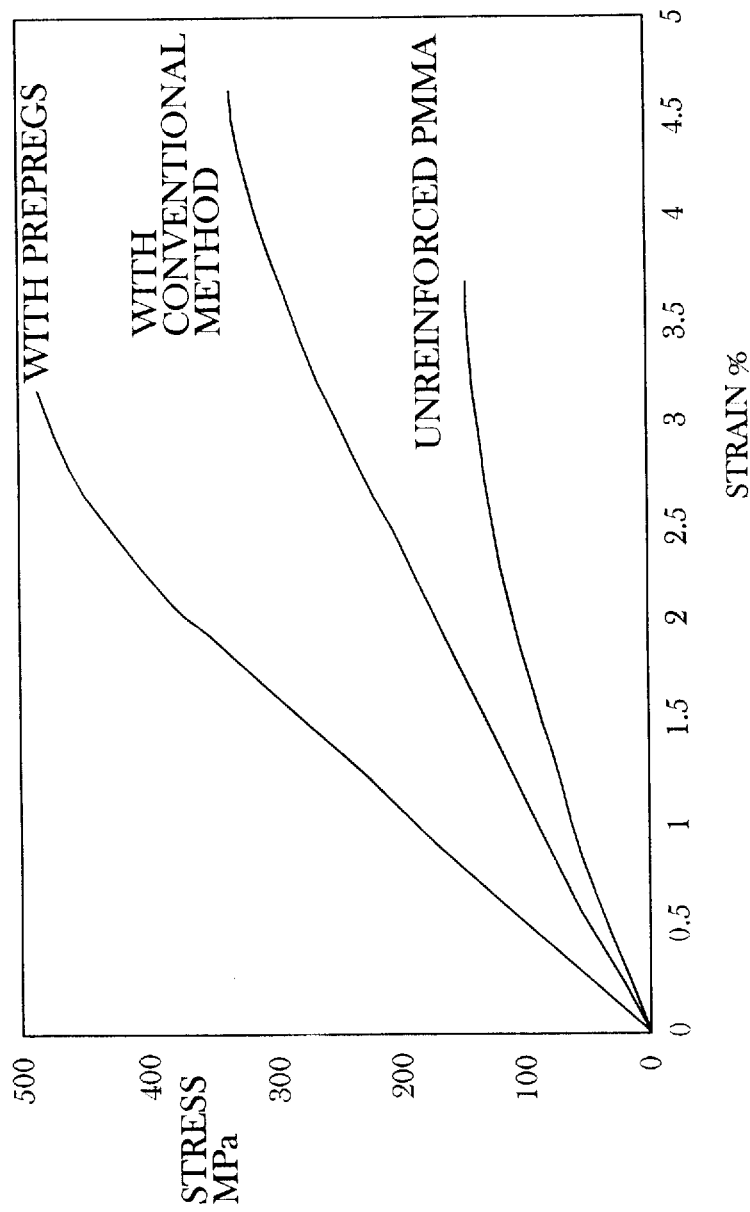
FIG. 3 shows the flexural properties of a GF-PMMA composite.

Flexural properties of the unidirectional glass fiber reinforced dental PMMA composite fabricated with the method described in prior art, and according to the present invention are shown in Table 1 and FIG. 3. The test specimens of the aforementioned test had a fibre concentration which could be easily used in the fabrication method of prior art and according to the present invention.

For the glass fibre reinforced removable partial dentures according to present invention, the fatigue resistance against the bending caused by the simulated force of the mastification (150N occusal force on 300 ms intervals in water at +37° C.) was 15 times higher than that of the traditional metal wire reinforced denture. The impact strength of the glass fibre reinforced dental PMMA according to the present invention was 70 kJ/M$^2$ measured by a Charpy-type impact tester (WPM Leipzig, Leipzig, Germany) which is considerably higher than that of the metal wire reinforced PMMA. The occlusal force required to fracture a three unit fixed partial denture made from dental PMMA was 91N. By reinforcing the three unit bridge with the prepregs according to this invention, the resistance of the bridge against the occlusal force increased to 350N.

The convertion of MMA to PMMA in the prepregs of glass fiber reinforced PMMA was as high as in the unreinforced PMMA tested by measuring the residual MMA release from the composite (high-performance-liquid-chromatography method, in accordance with the ISO 1567 standard). Water sorption and solubility of glass fiber reinforced PMMA were also in accordance with ISO specification.

TABLE 1

Flexural strength (MPa) and flexural modulus (GPa) of autopolymerizing PMMA and unidirectional GF-PMMA composite fabricated according conventional technique and according to the new prepreg technique (three-pont loading tests in accordance with ISO 1567 standards).

|  | Flexural strength | Flexural modulus |
|---|---|---|
| Unreinforced PMMA | 89.1 | 2.83 |
| GF-PMMA composite with conventional technique | 231.2 | 7.12 |
| GF-PMMA composite with prepreg technique | 335.0 | 12.56 |

It will be appreciated that the methods of the present invention can be incorporated in the form of a variety of embodiments, only a few of which are disclosed herein. It will be apparent for the specialist that other embodiments exist and do not depart from the spirit of the invention. Thus, the described embodiments are illustrative and should not be construed as restrictive.

REFERENCES

1. Smith D. C. The acrylic denture:mechanical evaluation midline fracture. Br Dent J 1961; 110:257–67.
2. Wetherell J. D., Smales R. J. Partial denture failures: A longterm clinical survey. J Dent 1980; 8:333–40.
3. Vallittu P. K., Lassila V. P., Lappalainen R. Number and type of damages of removable dentures in two cities of Finland. Acta Odontol Scand 1993; 51:363–5.
4. Darbar U. R., Huggett R., Harrison A. Denture fracture—a survey. Br Dent J 1994; 176:342–5.
5. Ruffino A. R. Effect of steel strengtheners on fracture resistance of the acrylic resin complete denture base. J Prosthet Dent 1985; 54:75–8.
6. Vallittu P. K. Effect of some properties of metal strengtheners on the fracture resistance of acrylic denture base material construction. J Oral Rehabil 1993; 20:241–8.
7. Schwickerath H. Werkstoffe in der Zahnheilkunde. Grundlagen, Verarbaeitung, Beanspruchung und Verhalten im klinischen Einsatz. Quintessence Publ. Berlin, 1977:189–94.
8. Vallittu P. K. Ultra-high-modulus polyethylene ribbon as reinforcement for autopolymerizing polymethyl methacrylate. A short communication. Dent Mater, in press.
9. Grave A. M. H., Chandler H. D., Wolfaardt J. F. Denture base acrylic reinforced with high modulus fibre. Dent Mater 1985; 1:185–7.
10. Vallittu P. K., Lassila V. P., Lappalainen R. Acrylic resin-fibre composite—Part I: The effect of fiber concentration on fracture resistance. J Prosthet Dent 1994; 71:607–12.
11. Williamson D. L., Boyer D. B., Aquilino S. A., Leary J. M. Effect of polyethylene fiber reinforcement on the strength of denture base resins polymerized by microwave energy. J Prosthet Dent 1994; 72:635–8.

12. Yaznadie N., Mahood M. Carbon fiber acrylic resin composite: an investigation of transverse strength. J Prosthet Dent 1985; 54:543–7.
13. Ladizesky N. H., Ho C. F., Chow T. W. Reinforcement of complete denture bases with continuous high performance polyethylene fibers. J Prosthet Dent 1992; 68:934–9.
14. Causton B. E. Denture base polymers and liners. In: O'Brien W. J. ed. Dental materials: Properties and selection. Quintessence Publ., Chicago, 1989:167–9.
15. Cogswell F. N. Components of a thermoplastic structural composite. In: Cogswell F. N. ed: Thermoplastic structural composites. Butterworth Heinemann, Oxford 1992:38–57.
16. Goldberg A. J., Burnstone C. J. The use of continuous fiber reinforcement in dentistry. Dent Mater 1992; 8:197–202.
17. Wylegala R. T. Reinforcing denture base material with carbon fibres. Dent Tech 1973; 26:97–100.
18. Ekstrand K., Ruyter I. E., Wellendorf H. Carbon/graphite fiber reinforced poly(methylmethacrylate): properties under dry and wet conditions. J Biomed Mater Res 1987; 21:1065–80.
19. Mullarky R. H. Aramid fiber reinforcement of acrylic appliances. J Clin Orthod 1985; 19:655–8.
20. Gutteridge D. L. The effect of including ultra-high-modulus polyethylene fibre on the impact strength of acrylic resin. Br Dent J 1988; 164:177–80.
21. Gutteridge D. L. Reinforcement of poly (methylmethacrylate) with ultra-high-modulus polyethene fibre. J Dent 1992; 20:50–4.
22. Ladizesky N. H., Chow T. W. The effect of highly drawn polyethylene fibres on the mechanical properties of denture base resins. Clin Mater 1990; 68:934–9.
23. Ladizesky N. H., Cheng Y. Y., Chow T. W., Ward I. M. Acrylic resin reinforced with chopped high performance polyethylene fiber properties and denture construction. Dent Mater 1993; 9:128–35.
24. Phillips R. W. Skinner's science of dental materials. W.B. Saunders Company, Philadelphia, 1982:170–3.
25. Winkler S. Essentials of complete denture prosthodontics. W.B. Saunders Company, Toronto, 1979:416–505.

I claim:

1. A method for the preparation of a prepreg comprising a fibre product pre-impregnated with a polymer, said prepreg being porous and easy to shape at room temperature after the addition of a plasticizer, wherein the method comprises either
   i)
      a) coating fibres with a powder comprising at least one polymer and optionally an agent having the ability to initiate a polymerization reaction of said polymer,
      b) adding to the composition obtained in step a) a solvent possessing the ability to dissolve said polymer but lacking the ability to initiate the polymerization reaction of said polymer, and
      c) evaporating the solvent, or
   ii)
      a) dissolving a powder comprising at least one polymer and optionally an agent having the ability to initiate a polymerization reaction of said polymer into a solvent possessing the ability to dissolve said polymer but lacking the ability to initiate the polymerization reaction of said polymer, and
      b) contacting the fibres with the solution obtained in the foregoing step, and
      c) evaporating the solvent.

2. The method according to claim 1 wherein the composition obtained in step i) a) is added to a mould before the solvent is added thereto.

3. A method for the preparation of a prepreg comprising a fibre product pre-impregnated with a polymer, said prepreg being porous and easy to shape at room temperature after the addition of a plasticizer, wherein the method comprises either
   i)
      a) coating fibres with a powder comprising at least one polymer and optionally an agent having the ability to initiate a polymerization reaction of said polymer,
      b) adding to the composition obtained in step a) a solvent possessing the ability to dissolve said polymer but lacking the ability to initiate the polymerization reaction of said polymer, and
      c) evaporating the solvent, or
   ii)
      a) dissolving a powder comprising at least one polymer and optionally an agent having the ability to initiate a polymerization reaction of said polymer into a solvent possessing the ability to dissolve said polymer but lacking the ability to initiate the polymerization reaction of said polymer, and
      b) contacting fibres with the solution obtained in the foregoing step, and
      c) evaporating the solvent, wherein a surface of the fibres is treated so as to facilitate bonding of the polymer to the fibres, whereafter the surface treated fibres are coated with the polymer powder.

4. The method according to claim 1, wherein the fibres comprise a glass fibre.

5. A method for the preparation of a prepreg comprising a fibre product pre-impregnated with a polymer, said prepreg being porous and easy to shape at room temperature after the addition of a plasticizer, wherein the method comprises either
   i)
      a) coating fibres with a powder comprising at least one polymer and optionally an agent having the ability to initiate a polymerization reaction of said polymer,
      b) adding to the composition obtained in step a) a solvent possessing the ability to dissolve said polymer but lacking the ability to initiate the polymerization reaction of said polymer, and
      c) evaporating the solvent, or
   ii)
      a) dissolving a powder comprising at least one polymer and optionally an agent having the ability to initiate a polymerization reaction of said polymer into a solvent possessing the ability to dissolve said polymer but lacking the ability to initiate the polymerization reaction of said polymer, and
      b) contacting fibres with the solution obtained in the foregoing step, and
      c) evaporating the solvent, wherein the polymer is selected from the group consisting of polymethyl methacrylate, ethyleneglycoldimethacrylate, 2,2-bis - propane, or hydroxyethylenemethacrylate, and wherein the agent facilitating the bonding of the polymer to the fibres is a silane compound which has been cured onto the fibres at elevated temperature.

6. A method for the manufacture of a fibre reinforced composite wherein a prepreg is used, said prepreg comprising a fibre product pre-impregnated with a polymer, wherein said polymer is present between the individual fibres and has been distributed between the fibres as a solution from which the solvent has been evaporated, said prepreg being porous and easy to shape at room temperature after the addition of a plasticizer, wherein the method comprises either i)
   a) coating fibres with a powder comprising at least one polymer and optionally an agent having the ability to initiate a polymerization reaction of said polymer,
   b) adding to the composition obtained in step a) a solvent possessing the ability to dissolve said polymer but lacking the ability to initiate the polymerization reaction of said polymer, and
   c) evaporating the solvent, or ii)
   a) dissolving a powder comprising at least one polymer and optionally an agent having the ability to initiate a polymerization reaction of said polymer into a solvent possessing the ability to dissolve said polymer but lacking the ability to initiate the polymerization reaction of said polymer, and
   b) contacting fibres with the solution obtained in the foregoing step, and
   c) evaporating the solvent, said method for the manufacture of a fibre reinforced composite comprising the steps of
      adding a plasticizer to said prepreg, which optionally can be pre-formed
      shaping the plasticized prepreg into a desired form,
      embedding the prepreg into the plain polymer of the composite or into a mixture of said polymer and the monomer, and
      allowing the polymer of the prepreg to polymerize simultaneously with the plain polymer of the composite.

7. The method according to claim 6 wherein the composite obtained in a further step is machined into one or more desired blocks or into desired form.

8. The method according to claim 6 wherein the plasticizer is the monomer of the polymer used in the prepreg.

9. The method according to claim 6, wherein the polymer of the prepreg is the same as the plain polymer of the composite.

10. The method according to claim 5, wherein said silane compound comprises gamma-methacryloxypropyltrimethoxysilane.

11. The method according to claim 1, wherein said solvent possessing the ability to dissolve said polymer but lacking the ability to initiate the polymerization reaction of said polymer is tetrahydrofuran.

12. A prepreg which is porous and easy to shape at room temperature after the addition of a plasticizer, said prepreg comprising fibres and a polymer wherein said polymer is present between the individual fibres and has been distributed between the fibres as a solution from which the solvent has been evaporated.

13. The prepreg according to claim 12 wherein the porous further comprises an agent having the ability to initiate polymerization reaction of said polymer.

14. The prepreg according to claim 12 wherein the fibres are in the form of a roving, woven roving, woven mat, chopped strand mat, short fibres, a whisker or particle formed, or a mixture of the aforementioned.

15. The prepreg according to claim 12, wherein the surface of the fibres has been treated so as to facilitate the bonding of the polymer.

16. The prepreg according to claim 12, wherein the fibres comprise a glass fibre, the polymer is selected from the group consisting of polymethyl methacrylate, ethyleneglycoldimethacrylate 2,2-bis-propane and hydroxyethylenemethacrylate; and a silane compound has been applied onto a surface of the fibres.

17. A fibre reinforced composite comprising a prepreg which is porous and easy to shape at room temperature after the addition of a plasticizer, said prepreg comprising fibres and a polymer wherein said polymer is present between the individual fibres and has been distributed between the fibres as a solution from which the solvent has been evaporated,
   wherein said prepreg has been plasticized by wetting with a monomer, shaped into a desired form and embedded into the plain polymer of the composite, and the polymer of said prepreg has been allowed to polymerize simultaneously with the plain polymer of the composite.

18. A composite according to claim 17 in the form of medical or dental constructs selected from the group consisting of prosthodontic, orthodontic and orthopaedic appliances; removable denture frameworks, removable denture clasps; precision attachments; permanent fixed prostheses; temporary fixed prostheses; dental implants; medical implants; root canal fillings of an endodontically treated tooth; posts, cores, fillings and crowns of the tooth; and mouth guards.

19. The prepreg according to claim 16, wherein said silane compound comprises gamma-methacryloxypropyltrimethoxysilane.

* * * * *